(12) United States Patent
Ambati et al.

(10) Patent No.: US 8,236,991 B2
(45) Date of Patent: Aug. 7, 2012

(54) PROCESS FOR THE PREPARATION OF SUBSTANTIALLY PURE (2S,3S,5S)-5-AMINO-2-N,N-DIBENZYLAMINO-3-HYDROXY-1,6-DIPHENYLHEXANE

(75) Inventors: V Raghava Reddy Ambati, Hyderabad (IN); Srinivas Garaga, Hyderabad (IN); Ramesh Dandala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 240 days.

(21) Appl. No.: 12/451,872

(22) PCT Filed: Jun. 5, 2008

(86) PCT No.: PCT/IB2008/001591
§ 371 (c)(1),
(2), (4) Date: Apr. 1, 2010

(87) PCT Pub. No.: WO2008/149228
PCT Pub. Date: Dec. 11, 2008

(65) Prior Publication Data
US 2010/0317855 A1    Dec. 16, 2010

(30) Foreign Application Priority Data
Jun. 8, 2007 (IN) ............................ 1184/CHE/2007

(51) Int. Cl.
*C07C 21/00* (2006.01)
*C07D 277/22* (2006.01)
*C07D 277/28* (2006.01)

(52) U.S. Cl. .................. 564/355; 548/203; 548/204

(58) Field of Classification Search .................. 564/355; 548/203–205
See application file for complete search history.

(56) References Cited

FOREIGN PATENT DOCUMENTS
WO    WO 2006/090264 A1  *  8/2006

OTHER PUBLICATIONS

Marc Loudon, separation using amine basicity, (Organic Chemistry textbook 3rd edition, 1995 pp. 1125-1126).*

* cited by examiner

*Primary Examiner* — Jafar Parsa
(74) *Attorney, Agent, or Firm* — Jay R Akhave

(57) ABSTRACT

The present invention relates to the purification of (2S,3S,5S)-5-amino-2-N,N-dibenzylamino-3-hydroxy-1,6-diphenylhexane (III) by making its crystalline acid addition salt, which can be used as such to produce Lopinavir/Ritonavir with high purity and yield. Formula III

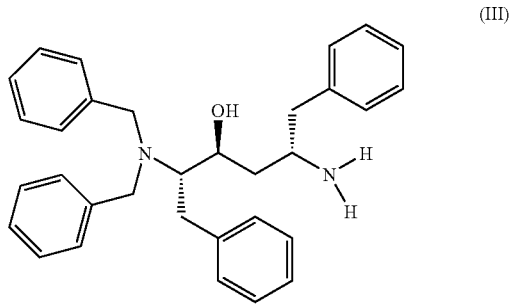

9 Claims, No Drawings

PROCESS FOR THE PREPARATION OF SUBSTANTIALLY PURE (2S,3S,5S)-5-AMINO-2-N,N-DIBENZYLAMINO-3-HYDROXY-1,6-DIPHENYLHEXANE

FIELD OF THE INVENTION

The present invention relates to an improved process for the preparation of substantially pure (2S,3S,5S)-5-amino-2-N,N-dibenzylamino-3-hydroxy-1,6-diphenylhexane of formula (III).

Formula III

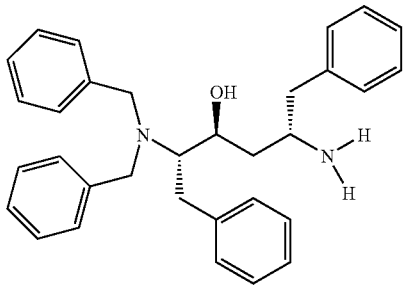

The compound of formula (III) is a key intermediate in the preparation of HIV protease inhibitors Lopinavir and Ritonavir of formula I and II respectively.

BACKGROUND OF THE INVENTION

Lopinavir is chemically known as (αS)-N-[(1S,3S,4S)-4-[[(2,6-dimethylphenoxy)acetyl]amino]-3-hydroxy-5-phenyl-1-(phenylmethyl)pentyl]tetrahydro-α-(1-methylethyl)-2-oxo-1(2H)-pyrimidineacetamide and structurally represented by Formula (I).

Formula I

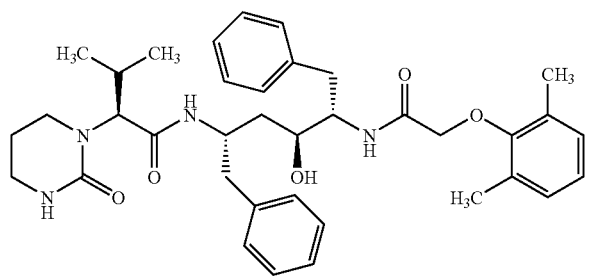

Ritonavir is chemically known as [5S-(5R*,8R*,10R*,11R*)]-10-Hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid 5-thiazolylmethyl ester and structurally represented by Formula II.

Formula II

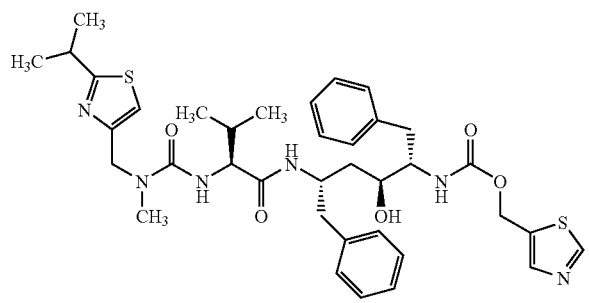

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, human T-cell lymphotrophic viruses, which cause human acute cell leukemia, and bovine and feline leukemia viruses which cause leukemia in domestic animals.

Lopinavir is known to have utility for the inhibition of HIV protease and the inhibition of HIV infection. However, Lopinavir is not effective for the treatment of HIV infection when administrated alone. Lopinavir is particularly effective for the inhibition of HIV protease and for the inhibition of HIV infection when co-administered with Ritonavir. Lopinavir, when combined with Ritonavir, is also particularly effective for the inhibition of HIV infection when used in combination with one or more reverse transcriptase inhibitors and/or one or more other HIV protease inhibitors. Lopinavir is indicated in combination with Ritonavir for the treatment of HIV-infection and is manufactured under the trade name of Kaletra®.

Ritonavir is an inhibitor of the HIV-1 and HIV-2 proteases with in vitro and in vivo activity against the Human Immunodeficiency Virus ("HIV"), and is presently sold in a soft gelatin capsule dosage form for oral administration under the trade name Norvir® and is indicated for use in combination with other antiretroviral agents for the treatment of HIV-infection.

(2S,3S,5S)-5-Amino-2-N,N-dibenzylamino-3-hydroxy-1,6-diphenylhexane (III) or an acid addition salt thereof is an useful intermediate for preparing compounds with antiviral activity such as Lopinavir and Ritonavir.

Formula III

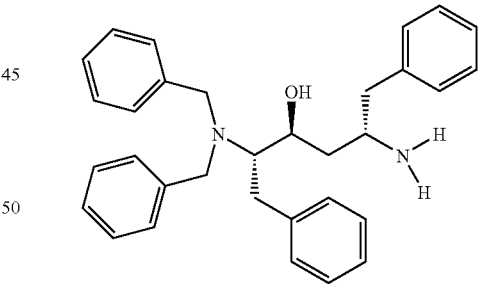

Abbott Laboratories has disclosed compound of Formula (III) in U.S. Pat. No. 5,491,253. U.S. Pat. No. 5,491,253 discloses a process for the preparation of (2S,3S,5S)-5-amino-2-N,N-dibenzylamino-3-hydroxy-1,6-diphenylhexane (III), which comprises, reducing (5S)-2-amino-5-N,N-dibenzylamino-4-oxo-1,6-diphenylhex-2-ene (IV) with sodium borohydride in presence of methane sulfonic acid to produce (2S,5S)-2-amino-N,N-dibenzylamino-4-oxo-1,6-diphenylhexane (V), which is further reduced using sodium borohydride in trifluoroacetic acid to produce (2S,3S,5S)-5-amino-2-N,N-dibenzylamino-3-hydroxy-1,6-diphenylhexane (III). The process is shown in the scheme-1.

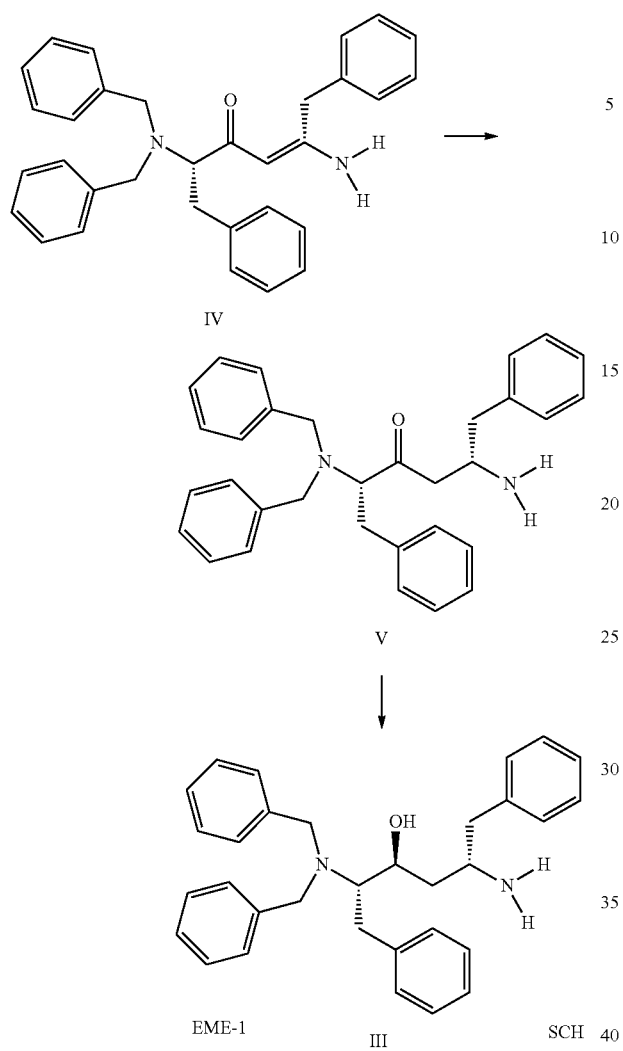

EME-1     III     SCH

Journal of Organic Chemistry 1995, 59, 4040-4041 discloses a similar process for the preparation of (2S,3S,5S)-5-amino-2-N,N-dibenzylamino-3-hydroxy-1,6-diphenylhexane (III) with optimized mole ratio of sodium borohydride and methane sulfonic acid to produce (2S,3S,5S)-5-amino-2-N,N-dibenzylamino-3-hydroxy-1,6-diphenylhexane (III) with diastereomeric mixture of 93:7.

Organic Process Research and Development 1999, 3, 94-100 also discloses a process for the preparation of (2S,3S,5S)-5-amino-2-N,N-dibenzylamino-3-hydroxy-1,6-diphenylhexane (III) using sodium tris(trifluoroacetoxy)borohydride and trifluoroacetic acid to produce (2S,3S,5S)-5-amino-2-N,N-dibenzylamino-3-hydroxy-1,6-diphenylhexane (III) diastereoselectively (84%) with 83% yield.

(2S,3S,5S)-5-Amino-2-N,N-dibenzylamino-3-hydroxy-1,6-diphenylhexane (III) prepared by the above prior-art processes is typically an oily mass and it is contaminated with undesired impurities, which are carried forward, as impurities, to the finished product Lopinavir/Ritonavir. Removal of these impurities in the final stage is often proved to be difficult and requires repeated crystallizations, which finally results in the low yield of Lopinavir and Ritonavir.

Hence, there is a need to develop a process, which provides (2S,3S,5S)-5-amino-2-N,N-dibenzylamino-3-hydroxy-1,6-diphenylhexane (III) a key intermediate in the preparation of Lopinavir and Ritonavir with essentially high purity.

The present invention specifically directs to the purification of (2S,3S,5S)-5-amino-2-N,N-dibenzylamino-3-hydroxy-1,6-diphenylhexane (III) by making its crystalline acid addition salt, which can be used as such to produce Lopinavir/Ritonavir with high purity and yield.

OBJECTIVE OF INVENTION

The main objective of the present invention is to provide a simple and cost-effective process for the preparation of substantially pure (2S,3S,5S)-5-amino-2-N,N-dibenzylamino-3-hydroxy-1,6-diphenylhexane (III) and its use in the preparation of Lopinavir and Ritonavir.

SUMMARY OF THE INVENTION

Accordingly, the present invention provides a method for the preparation of pure (2S,3S,5S)-5-amino-2-N,N-dibenzylamino-3-hydroxy-1,6-diphenylhexane (III), which comprises:

(i) treating the compound of Formula (III)

Formula III

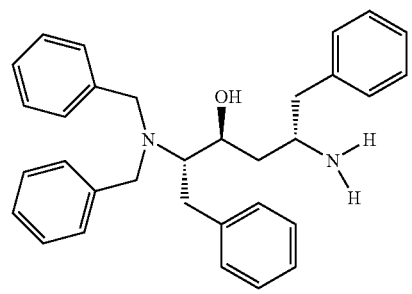

with an acid in a solvent to produce an acid addition salt of compound of Formula (IIIa)

Formula IIIa

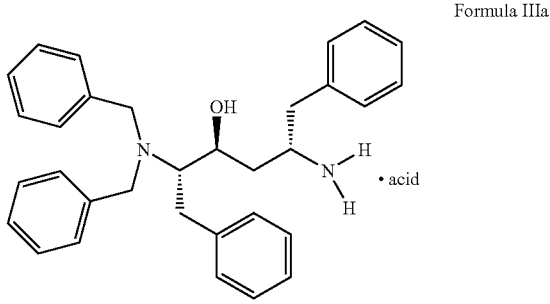

(ii) treating compound of formula (IIIa) with base in solvent to produce substantially pure compound of formula (III).

Formula III

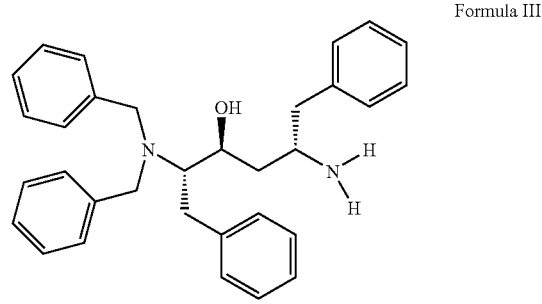

DETAILED DESCRIPTION OF THE INVENTION

The present invention relates to an improved process for the preparation of substantially pure (2S,3S,5S)-5-amino-2-N,N-dibenzylamino-3-hydroxy-1,6-diphenylhexane (III).

5-N,N-Dibenzylamino-4-oxo-1,6-diphenylhex-2-ene (IV) is reduced with reducing agent selected from metal hydrides such as sodium borohydride in presence of acid selected from organic acids such as methane sulfonic acid in a solvent ethyleneglycol dimethylether. The reaction is carried out at a temperature of about 0 to about −10° C. for about 18 hr to 24 hr. After completion of reaction, the reaction mass containing (2S,5S)-2-amino-N,N-dibenzylamino-4-oxo-1,6-diphenylhexane (V) can be used as such in the next step.

Reaction mass containing (2S,5S)-2-amino-N,N-dibenzylamino-4-oxo-1,6-diphenylhexane (V) is treated with reducing agent selected from metal hydrides such as sodium borohydride in presence of acid selected from organic acids such as trifluoro acetic acid in a solvent ethyleneglycol dimethylether. The reaction is carried out at a temperature of about 0 to about −20° C. for about ½ hr to 3 hr. After completion of reaction the reaction mass is quenched with basic reagent selected from aqueous sodium hydroxide. The reaction mass containing (2S,3S,5S)-5-amino-2-N,N -dibenzylamino-3-hydroxy-1,6-diphenylhexane (III) is extracted with a solvent selected from methyl tert -butylether and organic layer was separated and washed with sodium chloride solution. Organic layer is concentrated to residue to produce (2S,3S,5S)-5-amino-2-N,N-dibenzylamino-3-hydroxy-1,6-diphenylhexane (III).

(2S,3S,5S)-5-Amino-2-N,N-dibenzylamino-3-hydroxy-1,6-diphenylhexane (III) is treated with organic acid selected from L-pyroglutamic acid, succinic acid, fumaric acid, hydrochloric acid, sulfuric acid in a solvent selected from ethyl acetate, 1,4-dioxane, mixture of ethyl acetate and DMF at a temperature of about 55-60° C. After cooling to room temperature, the acid addition salt of (2S,3S,5S)-5-amino-2-N,N-dibenzylamino-3-hydroxy-1,6-diphenylhexane (IIIa) is precipitated in substantially pure form.

Acid addition salt of (2S,3S,5S)-5-amino-2-N,N-dibenzylamino-3-hydroxy-1,6-diphenylhexane (IIIa) obtained by the above process has a purity of above 90%. The major advantage realized with the process of the present invention is that the removal of undesired impurities and isolation of compound of formula (III) in a solid form, which otherwise would be possible without making acid addition salt of compound of Formula (III).

In another embodiment, the present invention also relates to the use of above acid addition salt of compound of Formula (III) to produce Lopinavir and Ritonavir.

Acid addition salt of (2S,3S,5S)-5-amino-2-N,N-dibenzylamino-3-hydroxy-1,6-diphenylhexane (IIIa) obtained by the above process is treated with the base selected from sodium bicarbonate, sodium carbonate, $K_2CO_3$, $KHCO_3$, KOH, NaOH, TEA in a solvent selected from ethyl acetate, dichloromethane, isopropyl acetate, to produce compound (III) which is further reacted with N-(2S-(1-tetrahydropyramid-2-onyl)-3-methylbutanoyl)imidazole (VI) to produce (2S,3S, 5S)-2-N,N-dibenzylamino -3-hydroxy-5-(2S-(1-tetrahydropyramid-2-onyl)-2-methylbutanoyl)amino-1,6-diphenylhexane of Formula (VII). The reaction is carried out at a reflux temperature for about 1 to 2 hr. After completion, the reaction mass is cooled to ambient temperature and washed with water and separate the organic layer. Organic layer is concentrated to produce (2S,3S,5S)-2-N,N-dibenzylamino-3-hydroxy-5-(2S-(1-tetrahydropyramid-2-onyl)-2-methylbutanoyl)amino-1,6-diphenylhexane of Formula (VII).

Compound of Formula (VII) is reduced over hydrogenation catalyst selected from Pd/C in presence of ammonium formate in a solvent selected from methanol. The reaction is carried out at a temperature of about 50 to 55° C. for about 1to 3 hrs. After completion of the reaction, catalyst is filtered and washed with methanol. The filtrate is concentrated to residue. The residue is again dissolved in a solvent selected from ethyl acetate, 1,4-dioxane, mixture of ethyl acetate and DMF and concentrated to reside to produce (2S,3S,5S)-2-amino-3-hydroxy-5-(2S-(1-tetrahydropyramid-2-onyl)-2-methylbutanoyl)-amino-1,6-diphenylhexane (VIII), which is further dissolved in a solvent selected from ethyl acetate, 1,4-dioxane and treated with an organic acid selected from L-pyroglutamic acid succinic acid, fumaric acid in a solvent selected from dimethylformamide (DMF), 1,4-dioxane to produce acid addition salt of compound of Formula (VIIIa).

Acid addition salt of compound of Formula (VIIIa) is treated with base selected from sodium bicarbonate in a solvent selected from ethyl acetate to produce compound of Formula (VIII), which is reacted with 2,6-dimethylphenoxyacetyl chloride (IX) at a temperature of about 20 to 30° C. for about 1 to 2 hr. After completion of reaction, the organic layer is separated and washed with sodium chloride solution. The organic layer is treated with carbon and concentrated under reduced pressure to residue. The residue containing Lopinavir is dissolved in solvent selected from ethyl acetate, isopropanol and isolated by adding an anti-solvent selected from heptanes, hexanes, and cyclohexane to produce Lopinavir crude. Lopinavir crude is further recrystallized from solvent selected from mixture of ethyl acetate & heptanes, ethyl acetate & hexanes, ethyl acetate & cyclohexane, IPA & heptanes, IPA & hexanes, IPA & cyclohexane, acetone & hexanes, acetone & heptanes, acetone & cyclohexane or toluene.

Ritonavir can also be prepared in an analogous manner, methods reported in literature, as described in U.S. Pat. No. 5,541,206.

The following examples to prepare compound of the present invention illustrate the nature of the invention and are provided for illustrative purpose only and should not be construed to limit the scope of the invention.

EXAMPLE

Stage-1

Preparation of (2S,3S,5S)-5-Amino-2-N,N-dibenzylamino-3-hydroxy-1,6-diphenylhexane 5-oxo-L-proline (IIIa)

Step-1: A suspension of sodium borohydride (23 g, 0.607 mol) in ethyleneglycol dimethylether (800 ml) was cooled to less than −5° C. and methanesulfonic acid (127 g, 1.32 mol) was added slowly keeping temperature below 0° C. After stirring for 30 min below 0° C., a solution of (5S)-2-amino-5-N,N-dibenzylamino-4-oxo-1,6-diphenyl-2-hexene (IV) (100 g, 0.217 mol) in a mixture of ethyleneglycol dimethylether (300 ml) and water (27.3 ml) was added while maintaining temperature below 0° C. The reaction mixture was further stirred for 20 h at 0-5° C.

Step-2: A mixture of sodium borohydride (23 g, 0.607 mol) and ethyleneglycol dimethylether (800 ml) was cooled to −10 to −5° C. and trifluoroacetic acid (123.7 g, 1.085 mol) was added while maintaining temperature between −10 to −5° C. Thereafter, temperature of reaction mass was raised to 10-15° C. and stirred for 30 min at the same temperature. The reaction mass from step-1 was added to the above mixture while maintaining the temperature below 20° C. and stirred at 15-20° C. for completion of the reaction. The reaction mass was cooled to 5-10° C. and quenched with 3N aq sodium hydroxide solution (700 ml). Methyl tert-butyl ether (1300 ml) was added and stirred for 10 min at 15-20° C. The organic layer was separated, washed with 20% aq. sodium chloride (2×400 ml) and concentrated at 45-50° C. under reduced pressure to get an oily mass, which was then dissolved in ethyl acetate (1000 ml) and heated to 55-60° C. Thereafter, L-pyroglutamic acid (23 g, 0.178 mol) was added to the reaction mass and stirred for 1 h at 55-60° C., whereupon the product precipitated. The resulting slurry was cooled to room temperature. Filtered the precipitated product, washed with ethyl acetate (200 ml) and dried at 50-55° C. under reduced pressure to yield the title compound as a white powder.

Yield: 100 g
Purity: 93% by HPLC
$^1$H NMR in DMSO-$d_6$ (δ in ppm): 1.12 (m, 1H), 1.86-1.96 (m, 2H), 2.04 (m, 2H), 2.12-2.27 (m, 2H), 2.62 (dd, 1H), 2.79-2.99 (m, 3H), 3.13 (m, 1H), 3.41-3.50 (m, 3H), 3.82 (dd, 1H), 4.07 (m, 2H), 7.11-7.33(m, 20H), 7.58 (brs, 1H).
Mass: MS (ESI$^+$) 465 (M+H)$^+$, MS (ESI) 463 (M−H)$^-$
IR (in Cm$^{-1}$): 3203, 3027, 1679, 1601, 1495, 1454, 1402, 1290.

Stage-2

Preparation of (2S,3S,5S)-2-N,N-dibenzylamino-3-hydroxy-5-(2S-(1-tetrahydropyrimid-2-onyl)-3-methylbutanoyl)amino-1,6-diphenylhexane(VII)

Step-1: N,N-Carbonyldiimidazole (34.14 g, 0.21 mol) was added to a suspension of 2S-(1-tetrahydropyrimid-2-onyl)-3-methylbutanoic acid (38.8 g, 0.194 mol) in ethyl acetate (200 ml) and the resulting solution was stirred for 1 h at 20-25° C. Thereafter, 1 ml of demineralized water was added to the reaction mass and further stirred for 15 min at 20-25° C.

Step-2: The compound obtained in Stage-1 (100 g, 0168 mol) was added to a mixture of ethyl acetate (500 ml), DM water (500 ml) and sodium bicarbonate (14.88 g) and stirred for 15 min at 25-30° C. After separation of layers the temperature of the organic layer was raised to reflux and reaction mass from step-1 of Stage-2 was added in 30 min while maintaining gentle reflux of the reaction mass. Thereafter, the reaction was stirred for 1 h at reflux temperature and cooled to room temperature. The reaction mass was washed with DM water (3×250 ml) and the organic layer separated. Evaporation of solvent from organic layer under reduced pressure at below 50° C. gave title product as an oily mass.

Stage-3

Preparation of (2S,3S,5S)-2-Amino-3-hydroxy-5-(2S-(1-tetrahydropyrimid-2-onyl)-3-methylbutanoyl)amino-1,6-diphenylhexane 5-oxo-L-proline salt (VIIIa)

The product obtained in Stage-2 (105 g, 0.162 mol) was dissolved in methanol (500 ml) and ammonium formate (31.92 g, 0.506 mol) followed by 5% Pd—C catalyst (10 g, 50% wet) were added. Thereafter, the temperature of reaction mass was raised to 50-55° C. and stirred for 2 h. The reaction mass was cooled to room temperature, filtered off the catalyst through hyflo and washed with methanol (100 ml). The combined filtrate was concentrated to dryness at 55-60° C. under reduced pressure and the resulting residue was dissolved in ethyl acetate (500 ml) at 50-55° C. and taken to dryness under reduced pressure to yield an oily residue. This residue was dissolved in a mixture of N,N-dimethylformamide (100 ml) and ethyl acetate (500 ml) at 50-55° C. A solution of L-pyroglutamic acid (19.3 g, 0.149 mol) in N,N-dimethylformamide (100 ml) was added and stirred the mass for 2 h at 50-55° C. during which time product precipitated. The reaction mass was cooled to room temperature and stirred for additional 5 h. The product was filtered and washed with a mixture of N,N-dimethylformamide (100 ml) and ethyl acetate (200 ml). The wet product was dried at 55-60° C. under reduced pressure (10-20 mm of Hg) for 8 h to produce the title compound.

Yield: 96 g

Stage-4

Preparation of (2S,3S,5S)-2-(2,6-dimethylphenoxyacetyl)amino-3-hydroxy-5-[2S-(1-tetrahydropyrimid-2-onyl)-3-methylbutanoyl]amino-1,6-diphenylhexane (Lopinavir)(I)

Step-1: Thionyl chloride (12.5 g, 0.105 mol) was added to a stirred suspension of 2,6-dimethylphenoxyacetic acid (15.12 g, 0.084 mol) in ethyl acetate (50 ml) followed by a drop of N,N-dimethylformamide. The reaction mixture was heated to 50° C. and stirred for an additional 2 h. The resulting acid chloride solution was cooled to 20-25° C. and held at this temperature for the coupling reaction (Step-2).

Step-2: The product obtained in Stage-3 (50 g, 0.084 mol) was added to a mixture of ethyl acetate (375 ml) and DM water (375 ml). Sodium bicarbonate (41.22 g, 0.49 mol) was added and stirred for 15 min at 20-25° C. Thereafter, the solution of acid chloride prepared in step-1 of Stage-4 was added in 10 min while maintaining a vigorous stirring at 20-25° C. After stirring for 1 h at 20-25° C., the organic layer was separated and washed with 5% aq sodium bicarbonate (250 ml) followed by 10% aq sodium chloride solution (250 ml). The organic layer was treated with activated carbon (5 g) for 15 min. The carbon was filtered off through hyflo and washed with ethyl acetate (50 ml). The combined filtrate was concentrated at 50-55° C. under reduced pressure to dryness and the resulting residue was dissolved in ethyl acetate (250 ml) and taken to dryness. The residue obtained was dissolved in ethyl acetate (250 ml) at 50-60° C. and added heptanes (250 ml). The reaction mass was stirred at 50-55° C. for an additional 1 h and the resulting slurry was cooled to room temperature. After stirring the crystallized product for 5 h at room temperature the product was isolated by filtration and washed with a mixture of ethyl acetate (50 ml) and heptanes (50 ml). The wet product was dried under reduced pressure at 50° C. to obtain 45 g of Lopinavir.

Purity of Lopinavir: 99.5% by HPLC

Comparative Example

Preparation of (2S,3S,5S)-2-(2,6-dimethylphenoxyacetyl)amino-3-hydroxy-5-[2S-(1-tetrahydropyrimid-2-onyl)-3-methylbutanoyl]amino-1,6-diphenylhexane (Lopinavir)(I)

Stage-1

Preparation of (2S,3S,5S)-5-Amino-2-N,N-dibenzylamino-3-hydroxy-1,6-diphenylhexane (III)

Step-1: A suspension of sodium borohydride (23 g, 0.067 mol) in ethyleneglycol dimethyl ether (800 ml) was cooled to less than −5° C. and methane sulfonic acid (127 g, 1.32 mol) was added slowly keeping temperature below 0° C. After stirring for 30 min below 0° C., a solution of (5S)-2-amino-5-N,N-dibenzylamino-4-oxo-1,6-diphenylhex-2-ene (IV) (100 g, 0.217 mol) in a mixture of ethyleneglycol dimethyl ether (300 ml) and water (27.3 ml) was added while maintaining temperature below 0° C. The reaction mixture was further stirred for 20 h at 0-5° C.

Step-2: A mixture of sodium borohydride (23 g, 0.607 mol) ethyleneglycol dimethyl ether (800 ml) was cooled to −10° to −5° C. and trifluoroacetic acid (123.7 g, 1.085 mol) was added while maintaining temperature between −10° to −5° C. Thereafter temperature of reaction mass was raised to 10-15° C. and stirred for 30 min at the same temperature. The reaction mass from step-1 was added to the above mixture while maintaining the temperature below 20° C. and continued the stirring at 15-20° C. for completion of the reaction. The reaction mass was cooled to 5-10° C. and quenched with 3N aqueous sodium hydroxide solution (700 ml). Methyl tert-butyl ether (1300 ml) was added and stirred for 10 min at 15-20° C. The organic layer was separated, washed with 20% aqueous sodium chloride (2×400 ml) and concentrated at 45-50° C. under reduced pressure to give 100 g of title compound as an oily mass. This oily mass can be used as such in the further stage.

Purity: 86% by HPLC

Stage-2

Preparation of (2S,3S,5S)-2-N,N-Dibenzylamino-3-hydroxy-5-(2S-(1-tetrahydropyramid-2-onyl)-2-methylbutanoyl)amino-1,6-diphenylhexane of Formula (VII)

Step-1: N,N-Carbonyl diimidazole (43.64 g, 0.269 mol) was added to a suspension of 2S-(1-tetrahydropyramid-2-onyl)-3-methylbutanoyl-3-methyl butanoic acid (49.56 g, 0.248 mol) in ethyl acetate (300 ml) and the resulting solution was stirred for 1 h at 20-25° C. Thereafter, 1 ml of demineralized water was added to the reaction mass and further stirred for 15 min at 20-25° C.

Step-2: The compound obtained in Stage-1 (100 g, 0.215 mol) was dissolved in mixture of ethyl acetate (400 ml) and DM water (10 ml). Temperature was raised to reflux and reaction mass from step-1 of Stage-2 was added in 30 min while maintaining gentle reflux of the reaction mass. Thereafter the reaction mass stirred for 1 h at reflux temperature and cooled to room temperature. The reaction mass was washed with DM water (3×500 ml) and the organic layer separated. Evaporation of solvent from the organic layer under reduced pressure at below 50° C. gave 115 g of title compound as an oily mass.

Stage-3

Preparation of (2S,3S,5S)-2-Amino-3-hydroxy-5-(2S-(1-tetrahydropyrimid-2-onyl)-3-methylbutanoyl) amino-1,6-diphenylhexane 5-oxo-L-proline salt (VIIIa)

The product obtained in Stage-2 (115 g, 0.178 mol) was dissolved in methanol (575 ml) and ammonium formate (33.67 g, 0.534 mol) followed by 5% Pd—C catalyst (15 g, 50% wet) were added. Thereafter, the temperature of reaction mass was raised to 50-55° C. and stirred for 2 h. The reaction mass was cooled to room temperature, filtered off the catalyst through hyflo and washed with methanol (100 ml). The combined filtrate was concentrated to dryness at 55-60° C. under reduced pressure and the resulting residue was dissolved in ethyl acetate (500 ml) at 50-55° C. and taken to dryness under reduced pressure to yield an oily residue. This residue was dissolved in a mixture of N,N-dimethylformamide (100 ml) and ethyl acetate (500 ml) at 50-55° C. A solution of L-pyroglutamic acid (21.67 g, 0.168 mol) in N,N-dimethylformamide (100 ml) was added and stirred the mass for 2 h at 50-55° C. during which time product precipitated. The reaction mass was cooled to room temperature and stirred for additional 5 h. The product was filtered and washed with a mixture of N,N-dimethylformamide (100 ml) and ethyl acetate (200 ml). The wet product was dried at 55-60° C. under reduced pressure (10-20 mm of Hg) for 8 h to produce the title compound.

Yield: 87 g

Stage-4

Preparation of (2S,3S,5S)-2-(2,6-dimethylphenoxyacetyl)amino-3-hydroxy-5-[2S-(1-tetrahydropyrimid-2-onyl)-3-methylbutanoyl]amino-1,6-diphenylhexane (Lopinavir)(I)

Step-1: Thionyl chloride (12.5 g, 0.105 mol) was added to a stirred suspension of 2,6-dimethylphenoxyacetic acid (15.12 g, 0.084 mol) in ethyl acetate (50 ml) followed by a drop of N,N-dimethylformamide. The reaction mixture was heated to 50° C. and stirred for an additional 2 h. The resulting acid chloride solution was cooled to 20-25° C. and held at this temperature for the coupling reaction (Step-2).

Step-2: The product obtained in Stage-3 (50 g, 0.084 mol) was added to a mixture of ethyl acetate (375 ml) and DM water (375 ml). Sodium bicarbonate (41.22 g, 0.49 mol) was added and stirred for 15 min at 20-25° C. Thereafter, the solution of acid chloride prepared in step-1 of Stage-4 was added in 10 min while maintaining a vigorous stirring at 20-25° C. After stirring for 1 h at 20-25° C., the organic layer was separated and washed with 5% aq sodium bicarbonate (250 ml) followed by 10% aq sodium chloride solution (250 ml). The organic layer was treated with activated carbon (5 g) for 15 min. The carbon was filtered off through hyflo and washed with ethyl acetate (50 ml). The combined filtrate was concentrated at 50-55° C. under reduced pressure to dryness and the resulting residue was dissolved in ethyl acetate (250 ml) and taken to dryness. The residue obtained was dissolved in ethyl acetate (250 ml) at 50-60° C. and added heptanes (250 ml). The reaction mass was stirred at 50-55° C. for an additional 1 h and the resulting slurry was cooled to room temperature. After stirring the crystallized product for 5 h at room temperature the product was isolated by filtration and washed with a mixture of ethyl acetate (50 ml) and heptanes (50 ml). The wet product was dried under reduced pressure at 50° C. to obtain 45 g of Lopinavir.

Purity: 98.5% by HPLC

Step-3: The product obtained in Step-2 was further purified by recrystallization from a mixture of ethyl acetate (225 ml) and heptanes (225 ml) to get 40 g of pure Lopinavir.

Purity of Lopinavir: 99.5% by HPLC

We claim:
1. A process for the preparation of pure (2S,3S,5S)-5-amino-2-N,N-dibenzylamino-3-hydroxy-1,6-diphenylhexane (III), which comprises:
(i) reacting the compound of Formula (III)

Formula III

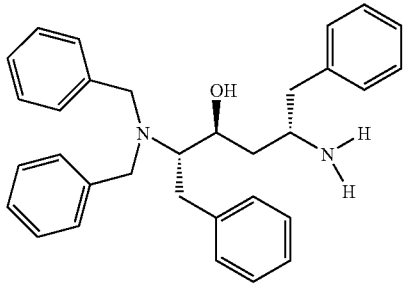

with an acid in a solvent to produce an acid addition salt of compound of Formula (IIIa);

Formula IIIa

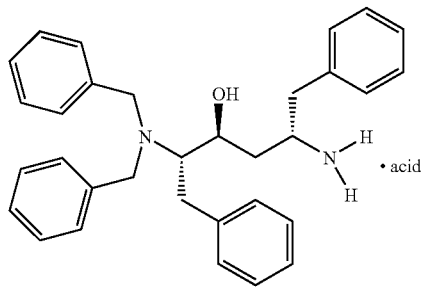

(ii) treating compound of formula (IIIa) with base in solvent to produce substantially pure compound of formula (III).

2. A process according to claim 1, wherein the acid is organic acid selected from L-pyroglutamic acid, succinic acid, fumaric acid.

3. A process according to claim 1, wherein the acid is inorganic acid selected from hydrochloric acid, sulfuric acid.

4. A process according to claim 1, wherein the solvent used in step (i) is selected from ethyl acetate, 1,4-dioxane, DMF.

5. A process according to claim 4, wherein the solvent is mixture of ethyl acetate and DMF.

6. A process according to claim 1, wherein the base used in step (i) is selected from sodium bicarbonate, sodium carbonate, $K_2CO_3$, $KHCO_3$, KOH, NaOH, TEA.

7. A process according to claim 1, wherein solvent used in step (i) is selected from ethyl acetate, dichloromethane, isopropyl acetate.

8. A process as claimed in claim 1, wherein the pure compound of formula (III) is converted to Lopinavir.

9. A process as claimed in claim 1, wherein the pure compound of formula (III) is converted to Ritonavir.

* * * * *